United States Patent [19]

Buysch et al.

[11] 4,073,746

[45] Feb. 14, 1978

[54] MIXTURES OF α,α'-BIS-(2-HYDROXY-3,5-DIALKYL-PHENYL)-P-AND -M-DIISOPROPYLBENZENES, A PROCESS FOR THE PREPARATION THEREOF AND THE USE THEREOF AS STABILIZERS

[75] Inventors: Hans-Josef Buysch, Krefeld; Harald Oertel, Odenthal-Gloebusch; Ernst Roos, Odenthal-Osenau, all of Germany

[73] Assignee: Bayer Aktiengesellschaft, Leverkusen-Bayerwerk, Germany

[21] Appl. No.: 688,146

[22] Filed: May 20, 1976

[30] Foreign Application Priority Data

May 24, 1975 Germany .............................. 2523106

[51] Int. Cl.$^2$ .............................................. C09K 15/08
[52] U.S. Cl. ..................................... 252/404; 252/407
[58] Field of Search ........................... 252/404 X, 407; 260/619, 619 B, 45.95, 77.555

[56] References Cited

U.S. PATENT DOCUMENTS 2,944,086  7/1960  Coffield et al. ...................... 252/404
3,057,928  10/1962  Koblitz et al. ...................... 260/619 A
3,778,409  12/1973  Oertel ............................. 260/45.8 NT

FOREIGN PATENT DOCUMENTS 2,012,285  5/1965  Germany ............................. 260/619

*Primary Examiner*—Benjamin R. Padgett
*Assistant Examiner*—Josephine Lloyd
*Attorney, Agent, or Firm*—Plumley and Tyner

[57] ABSTRACT

The invention relates to mixtures of α,α'-bis-(2-hydroxy-3,5-dialkylphenyl)-m-diisopropylbenzene and α,α'-bis-(2-hydroxy-3,5-dialkylphenyl)-p-diisopropylbenzene which contain at least 20% by weight and preferably from 40 to 70% by weight of the m-compound. Moreover, the invention relates to a process for the production of such mixtures. The mixtures are suitable for stabilizing polyurethanes and other synthetic polymers against discoloration and degradation when exposed to visible and/or UV light and/or atmospheric constituents such as oxygen oxides or nitrogen and waste gases from combustion. Particularly, they are suitable for stabilizing threads and foils of these products including coatings.

8 Claims, No Drawings

MIXTURES OF α,α'-BIS-(2-HYDROXY-3,5-DIALKYLPHENYL)-P-AND -M-DIISOPROPYLBENZENES, A PROCESS FOR THE PREPARATION THEREOF AND THE USE THEREOF AS STABILIZERS

This invention relates to mixtures of α,α'-bis-(2-hydroxy-3,5-dialkylphenyl)-p-diisopropylbenzenes and α,α'-bis-(2-hydroxy-3,5-dialkylphenyl)-m-diisopropylbenzenes, a process for preparing such mixtures.

The preparation of α,α'-bis-(2-hydroxy-3,5-dialkylphenyl)-p-diisopropylbenzenes by the reaction of α,α'-dihydroxy-p-diisopropylbenzene with 2,4-dialkylphenols in the presence of acid catalysts has been disclosed in German OS No. 2,012,285, but preparation from the corresponding m-diisopropylbenzene derivatives and from mixtures of the m- and p-compounds has not previously been described.

α,α'-dihydroxydiisopropylbenzenes may be obtained by atmospheric oxidation of diisopropylbenzenes, but when benzene is propylated, cumene, m- and p-diisopropylbenzene and higher propylated benzenes are obtained simultaneously. Although these higher propylated benzenes and cumene may easily be separated from diisopropylbenzene, m- and p-diisopropylbenzene may only be separated with great difficulty from each other by distillation. p-diisopropylbenzene is therefore much more expensive than a mixture of m- and p-diisoproplbenzene and it became necessary to attempt to replace p-diisopropylbenzene by mixtures of m- and p-diisopropylbenzene and hence to replace α,α'-bis(2-hydroxy-3,5-dialkylphenyl)-p-diisopropylbenzenes by mixtures of the corresponding p- and m-compounds.

In German OS No. 2,012,285, various strong acids, e.g. phosphoric acid, sulphuric acid, hydrochloric acid and p-toluenesulphonic acid, are indicated as catalysts for the conversion of α,α'-dihydroxy-p-diisopropylbenzene to α,α'-bis-(2-hydroxy-3,5-dialkylphenyl)-p-diisopropylbenzene. If mixtures of α,α'-dihydroxy-m- and -p-diisopropylbenzene. If mixtures of α,α'-dihydroxy-m- and -p-diisopropylbenzene are reacted with 2,4-dialkylphenols in accordance with the said process, no matter which of the above-mentioned acids used as catalyst, much lower yields are obtained and the end products consist of mixtures which are practically incapable of crystallizing and therefore very difficult to purify. Purification would be essential in this process since the crude products obtained, particularly when using p-toluene-sulphonic acid which is the preferred catalyst according to the above-mentioned German OS, is deep brown in colour. The most serious disadvantage, however, is that the mixtures obtained by this process have a much weaker stabilizing effect on polyurethanes than pure p-compounds.

It is an object of the present invention to avoid the afore-mentioned disadvantages. It has now surprisingly been found that this object is accomplished by the reaction of mixtures of α,α'-dihydroxy-m- and -p-diisopropylbenzene with 2,4-dialkylphenols which results in high yields of readily crystallizable products if gaseous hydrogen chloride is used as catalyst.

The present invention therefore relates to a process for the preparation of readily crystallizable mixtures of α,α'-bis-(2-hydroxy-3,5-dialkylphenyl-m-diisopropylbenzenes and α,α'-bis-(2-hydroxy-2,5-dialkylphenyl)-p-diisopropylbenzenes by the reaction of a mixture α,α'-dihydroxy-m- and -p-diisopropylbenzenes with an excess of 2,4-dialkylphenols in the presence of hydrogen chloride which is not bound to water.

The process according to the present invention may be carried out intermittently or continuously. A preferred and technically simple method consists of dissolving or suspending α,α'-dihydroxy-diisopropylbenzene in dialkyl phenol and introducing hydrogen chloride into this mixture. Alternatively, a solution of α,α'-dihydroxy-diisopropylbenzene in 2,4-dialkylphenol may be introduced into a saturated solution of hydrogen chloride in the same dialkylphenol. For a continuous process, the reactants are mixed and the reaction is then completed, for example in a tube reactor attached to the mixing apparatus.

The reaction must be carried out with an excess of 2,4-dialkylphenol. The molar ratio of α,α'-dihydroxy-diisopropylbenzene to dialkylphenol should be at least 1:3 and preferably from 1:5 to 1:12. Solvents which are inert under the reaction conditions, such as methylene chloride, chloroform, benzene, toluene, xylene, chlorobenzene or other petroleum hydrocarbons, may be used, but they are not essential.

Hydrogen chloride must be used in sufficient quantity so that it is freely available in the reaction mixture over and above the amount which is bound as hydrochloric acid by the water produced in the reaction. If this is not the case, the hydrochloric acid determines the course of the reaction which would not then lead to the desired products. The required condition is most easily fulfilled by saturating the reaction mixture with hydrogen chloride.

The reaction temperature employed is not particularly critical and may lie within a range of from 0 to 100° C and is preferably from 20 to 70° C. Lower temperatures reduce the reaction velocity, while higher temperatures promote side reactions.

The reaction products are easily isolated, for example, by distilling excess dialkylphenol from the reaction mixture. The sump product obtained is in many cases sufficiently pure to be used directly as stabilizer. If further purification is desired, the product may be recrystallized from a suitable solvent.

If desired, the solvent may be added right from the start, and after the reaction the excess acid may be washed out with water at an elevated temperature and the reaction mixture left to cool and the crystalline material collected. the mother liquor may be used again immediately if desired.

Suitable starting materials for the process according to the present invention are, on the one hand, mixtures of α,α'-dihydroxy-m- and -p-diisopropylbenzenes containing at least 20%, by weight, and preferably from 40 to 70%, by weight, of the m-compound, and, on the other hand, 2,4-dialkylphenols which may be substituted by, for example, ethyl, n-propyl, isopropyl, n-butyl, secondary butyl, amyl, isoamyl, hexyl, isohexyl, isooctyl, isononyl, 4-methylcyclohexyl, α-methylcyclohexyl, benzyl, α-methylbenzene or α,α-dimethylbenzyl, but particularly by methyl, tert.-butyl, cyclopentyl or cylohexyl. Those 2,4-dialkylphenols which carry a methyl group in the p-position are preferred.

As mentioned above, the mixtures according to the present invention and α,α'-(2-hydroxy-3,5-dialkylphenyl)-m-diisopropylbenzenes have not previously been described. Judging from the properties of the pure p-compounds, it was not to be expected that the mixtures would have the advantages mentioned above. On the contrary, the investigations mentioned above which were carried out on mixtures prepared according to German OS No. 2,012,285 indicated that the addition of m-compound would seriously impair the stabilizing effect and that the mixtures obtained would be of no practical use.

It must therefore be regarded as very surprising that mixtures with such highly advantageous properties could be obtained by the process according to the present invention. Firstly, it must be said that it was surprising to find that all the catalysts mentioned in German OS No. 2,012,285, even hydrochloric acid, which differs less than any of the others from the catalyst used according to the present invention, result in practically equally low yields of mixtures of poor quality. It was therefore to be expected that $\alpha,\alpha'$-dihydroxy-p-diisopropylbenzene would result in an end product with improved properties also when used in the presence of hydrogen chloride. This was remarkably found not to be the case. The yield of bis-phenol and its quality differ in no way from the yield and quality of bisphenol obtained with the other catalysts. This means that hydrogen chloride takes up a special position only in connection with the mixtures.

Although Belgian Pat. No. 614,663 disclosed a process of synthesizing $\alpha,\alpha'$-bis-(4-hydroxyphenyl)-diisopropylbenzenes from $\alpha,\alpha'$-dihydroxy-diisopropylbenzenes with the aid of hydrogen chloride, it only mentions hydrogen chloride together with other catalysts which may be used equally successfully. It gives no indication that the situation is the same when alkylating 2,4-substituted phenols as when alkylating phenols which are free in the para-position and still less does it give any indication that mixtures of $\alpha,\alpha'$-dihydroxy-m- and -p-diisopropylbenzene would behave in an anomalous manner.

The mixtures according to the present invention are at least equally good in their stabilizing qualities as the pure p-compounds while in other properties they are superior. Owing to their higher solubility, they may be more readily incorporated in polyurethanes and will not undergo any further crystallization in them as is occasionally observed in the case of p-compounds. This solid phase separation reduces the surface gloss of polyurethane products, a phenomenon which is particularly noticeable in products, such as fibres, which have a large surface area.

A further object of the present invention are mixtures of $\alpha,\alpha'$-bis-(2-hydroxy-3,5-dialkylphenyl)-m-diisopropylbenzene and $\alpha,\alpha'$-bis-(2-hydroxy-3,5-dialkylphenyl)-p-diisopropylbenzene which contain at least 20 %, by weight, and preferably from 40 to 70 %, by weight, of the m-compound. Mixtures of $\alpha,\alpha'$-bis-(2-hydroxy-3,5-dimethylphenyl)-p-diisopropylbenzene and $\alpha,\alpha'$-bis-(2-hydroxy-3,5-dimethylphenyl)-m-diisopropylbenzene are preferred.

Mixtures of $\alpha,\alpha'$-bis-(2-hydroxy-3,5-dialkylphenyl)-p-diisopropylbenzene and $\alpha,\alpha'$-bis-(2-hydroxy-3,5-dialkylphenyl)-m-diisopropylbenzene are used for stabilizing polymers, in particular polyethers, such as polytetrahydrofuran, polypropylene oxides, polyethylene oxides with OH end groups and for stabilizing derivatives thereof, such as esters, urethanes and amides. The mixtures are also used for stabilizing polycondensation products (such as polyamides, polyesters or mixtures thereof or mixtures of the polyamides or polyesters with additives) and for stabilizing polymerisation products and polyaddition products, such as polymers based on polyisocyanates or epoxides.

Lastly, the present invention relates, in particular, to mixtures of $\alpha,\alpha'$-bis-(2-hydroxy-3,5-dialkylphenyl)-m- and -p-diisopropylbenzenes for stabilizing polyurethanes against discoloration and degradation when exposed to visible and/or UV light and/or atmospheric constituents (such as oxygen, oxides of nitrogen and waste gases from combustion), particularly for stabilizing threads and foils of these products, including coatings.

The elastic polyurethanes which are required to be stabilized and which may in some cases be in the form of foams may be produced by conventional processes and from conventional starting materials. The polyurethanes are generally prepared by any of numerous well known and modifiable processes in which higher molecular weight polyhydroxyl compounds (e.g. polyesters or polyethers having a molecular weight of from 500 to 5,000 and a melting point preferably below 60° C) are reacted with aliphatic, araliphatic or aromatic polyisocyanates (preferably aromatic diisocyanates, such as tolylene diisocyanate or diphenylmethane-4,4'-diisocyanate) and so-called "chain lengthening agents", i.e. low molecular weight compounds (molecular weight e.g. from 18 to 400) which contain two or more groups capable of reacting with isocyanate groups (e.g. water, low molecular weight diols, diamines, dihydrazides or similar compounds, e.g. amino alcohols, amino hydrazides, hydroxy hydrazides, amino semicarbazides, semicarbazidohydrazides, semicarbazidocarbazic esters or mixtures of these chain lengthening agents) in one or more stages with or without solvent.

The following are mentioned as examples of starting materials: polyesters of adipic acid and dihydricalcohols containing from 2 to 10 carbon atoms, preferably more than 5 carbon atoms, the dihydricalcohols optionally also being used as mixtures in order to lower the melting points of the polyesters: polyesters of caprolactone and dihydricalcohols, polyalkylene ether diols, specifically polytetramethylene ether diols, polytrimethylene ether diols, polypropylene glycol or copolyethers thereof. The diisocyanates used are preferably aromatic diisocyanates, such as diphenylmethane-4,4'-diisocyanate, tolylene diisocyanate, araliphatic diisocyanates, such as m-xylylene diisocyanate, or aliphatic diisocyanates, such as hexamethylene diisocyanate and dicyclohexylmethane-4,4'-diisocyanate. These starting materials, if desired together with additional dihydric alcohols, are converted into isocyanate prepolymers which preferably have the structures indicated in Belgian Pat. No. 734,194. The following are examples of suitable chain lengthening agents, which may, if desired, be used as mixtures or reacted stepwise: water and/or dihydric or trihydric alcohols, such as butane diol and p-xylylene glycols, trimethylolpropane, amino alcohols, such as ethanolamine, diamines, such as diphenylmethane-4,4'-diamine and 3,3'-dichlorodiphenylmethane-4,4'-diamine. It is preferred, however, to use aliphatic diamines, such as ethylene diamine, 1,2-propylene diamine, isophorone diamine, metaxylylene diamine and hydrazine or dihydrazides, such as carbodihydrazide, oxalic acid dihydrazide, glutaric acid dihydrazide, pimelic acid dihydrazide and terephthalic acid dihydrazide or semicarbazido hydrazides, such as $\beta$-semicarbazide-alanyl hydrazide. These chain lengthening agents may, if desired, be used as mixtures.

The products are preferably used for stabilizing polyurethanes which, in addition to urethane groups, contain —NH—CO—NH— groups formed by the reaction of isocyanate groups with water and/or with compounds containing NH₂ end groups (e.g. diamines, dihydrazides, carbodihydrazide, semicarbazidohydrazides or hydrazine), and which have a substantially linear, segmented molecular structure, are soluble in highly polar solvents, such as dimethylformamide or dimethyl acetamide, before they are shaped and have characteristic segments which may be represented by the following general formula:

This segment may be obtained by the reaction of an isocyanate prepolymer OCN.Y.NCO with a chain lengthening agent H₂N.X.NH₂.

The group Y of the isocyanate prepolymer may, for example have the following structure:

or it may have some other, commonly occurring composition (see Belgian Pat. No. 734,194).

In the above formula, R represents a divalent aliphatic, araliphatic or aromatic residue )of a diisocyanate), D represents the residue of a high molecular weight polyhydroxyl compound having a molecular weight of from 500 to 5000 and a melting point below 60° C without its hydroxyl end groups (e.g. the residue of a polyalkylene ether, polyester, polyacetal or poly-N-alkylurethane). X represents the residue of a divalent chain lengthening agent which contains NH₂ end groups, without the said NH₂ end groups, e.g. an aliphatic, araliphatic, aromatic or heterocyclic residue, a HN—CO—alkylene—CO—NH residue, an NH—CO—NH—(CH₂)₂—CO—NH residue or a bond between two nitrogen atoms. The synthesis of such polyurethane (urea) has been described in detail, for example in German Auslegeschrift No. 1,270,276 and in Belgian Pat. No. 734,194. Polyurethane foams, for example, may be prepared by conventional processes and from conventional formulations with the addition of the stabilizers to the starting components (e.g. polyethers) (see for example, Kunststoff Handbuch, Volume VII, Polyurethane, Carl Hanser Verlag Munchen, 1966, pages 440 to 457 and 504 to 531).

The stabilizers may be incorporated with the polyurethanes by any methods suitable for the technical requirements of the process. A very simple method consists of adding the stabilizers, if desired as solutions, to solutions of the polyurethanes, for example to the polyurethane solutions in highly polar solvents, such as dimethylformamide or dimethylsulphoxide, which are the ones most preferably used for spinning, coating and coagulation purposes. Alternatively, the stabilizers may be worked into the melts or plasticized polyurethane sheets by means of suitable mixing devices, such as kneaders or rollers. In the case of elastomer threads, the stabilizers may, if desired, be applied to their surface together with the finish.

Another method of incorporating the stabilizers consists of adding them to the starting materials used for the preparation of the polyurethanes before polyurethane synthesis is carried out. Bisphenol compounds, are soluble for example, in high molecular weight polyhydroxyl compounds (e.g. polyesters or polyethers). These polyesters or polyethers already containing stabilizers may then be used for suitable polyurethane syntheses, for example for the production of foams or elastomers. The stabilizers may also be added to diisocyanates or to isocyanate prepolymers obtained from higher molecular weight polyhydroxyl compounds and diisocyanates (used in excess molar quantities) before the polyurethane product is produced, for example by spinning it into aqueous diamine solution. Discoloration of the polyurethanes may already be prevented at the stage of their synthesis by adding the stabilizers when the isocyanate prepolymers are being reacted with chain lengthening agents, such as diamines, hydrazine, hydrazides, or similar chain lengthening agents, in highly polar solvents, such as dimethylformamide or dimethylacetamide. The quantity of stabilizers added ranges from 0.01 to 10%, by weight, and is preferably from 0.1 to 5% by and most preferably from 0.3 to 3%, by weight.

The protection against light is found to be further increased by addition of the stabilizers according to the present invention to polyurethanes which contain from 0.02 to 1 mol, preferably from 0.05 to 0.3 mol of reactants with tertiary, aliphatically substituted amino groups, based on 1 kilogram of elastomer substance. Suitable reactants of this type include, for example, glycols, diamines, dihydrazides, polyesters or polyethers with tertiary amino groups, e.g. N,N-bis-(β-hydroxypropyl)-methylamine, N,N'-bis-(β-hydroxyethyl)-piperazine, N,N'-dimethyl-N,N'-bis-(γ-aminopropyl)-ethylenediamine, N,N'-bis-(γ-aminopropyl)-piperazine or polyethers which contain tertiary amino groups or polyesters which contain tertiary amino groups and which are prepared from dihydricalcohols containing tertiary amino groups.

The following experiments illustrate the connections explained above, using 2,4-dimethylphenyl as non-limiting example. "Parts" are parts on weight basis.

The following Examples are to further illustrate the invention without limiting it.

Comparison Example 1

This Example shows that p-toluenesulphonic acid used as catalyst provides high yields of bisphenol when used with α,α'-dihydroxy-p-diisopropylbenzene, but poor yields when used with an isomeric mixture.

a. A solution of 1164 g (6 mol) of a α,α'-dihydroxy-p-diisopropylbenzene in 5490 g (45 mol) of 2,4-dimethylphenol is added dropwise with stirring to a solution of 1830 g (15 mol) of 2,4-dimethylphenol over a period of from 9 to 10 hours at 150° C under an atmosphere of nitrogen. From 200 to 210 g of water evaporate off during this time. The reaction mixture is then stirred for a further 15 minutes, the catalyst is neutralised with 6.5 g of sodium carbonate, and 2,4-dimethylphenyl is removed by distillation at reduced pressure until the sump temperature reaches 140° C at 12 Torr. A light coloured, crystalline residue is obtained in a quantity of 2230 g = 93% of the theoretical yield. α,α'-bis-(2-hydroxy-3,5-dimethylphenyl)-p-diisopropylbenzene is obtained in 80% yield (melting point 179° C) when 100 g of the residue are recrystallised from 150 ml of tetrachloroethane.

b. If the same procedure is adopted with a mixture of about 60% of α,α'-dihydroxy-m-diisopropylbenzene and about 40% of -p-diisopropylbenzene, the residue obtained after removal of excess 2,4-dimethylphenol by distillation consists of 1410 g = 59% of the theoretical yield of a dark brown resin which does not crystallise and cannot by crystallised even by treatment with various solvents (tetrachloroethane, toluene, xylene, mineral spirits).

Comparison Example 2

Poor yields are also obtained with phosphoric acid and hydrochloric acids when an isomeric mixture of α,α'-dihydroxy-diisopropylbenzene is used.

a. The same procedure is employed as in Comparison Example 1, but using 25 g of concentrated phosphoric acid instead of p-toluenesulphonic acid and neutralizing with the corresponding quantity of base after the reaction. Only 950 g = 37% of the theoretical yield of a light coloured, non-crystallizable resin are obtained.

b. The reaction mixture and procedure differ in the following respects from those employed in comparison Example 1: 400 g of 20% hydrochloric acid are used instead of p-toluene sulphonic acid. The condensation temperature is maintained at from 90° to 95° C on account of the boiling point of hydrochloric acid, and no water is distilled off. After the reaction, hydrochloric acid and dimethylphenol are distilled off without previous neutralisation. Yield: 1395 g = 58% of the theoretical yield of a light brown, non-crystallizable resin.

EXAMPLE 1

This Example demonstrates that when hydrogen chloride is used as catalyst with an isomeric mixture of α,α'-dihydroxy-diisopropylbenzene, it differs from the catalysts previously used in that it brings about an excellent improvement in the yield and quality of the reaction product, but when used with α,α'-dihydroxy-p-diisopropylbenzene it does not differ from other catalysts.

a. A solution of 194 g (1 mol) of a mixture of about 60% of α,α'-dihydroxy-m-diisopropylbenzene and about 40% of α,α'-dihydroxy-p-diisopropylbenzene in 611 g (5 mol) of 2,4-dimethylphenol is added dropwise with stirring in the course of 1 hour to another 611 g of 2,4-dimethylphenol which has been saturated with hydrogen chloride at 50° C, and at the same time sufficient hydrogen chloride is passed through the reaction mixture to keep it saturated. The temperature during this procedure is maintained at from 50° to 60° C. After a further 2 hours under these conditions, hydrogen chloride, hydrochloric acid and excess 2,4-dimethyl phenol are distilled off in a water-jet vacuum until the sump temperature is from 180° to 190° C. A yellow oil which crystallises on cooling is obtained in a yield of 384 g = 95.5% of the theoretical yield. 322 g = 80% of the theoretical yield of colourless crystals (melting point from 135 to 179° C) are left after recrystallisation from 1.6 l of mineral spirits.

(b) If the same procedure is employed as in Example 1(a), but using α,α'-dihydroxy-p-diisopropylbenzene instead of the isomeric mixture, the yield of crude product is 372 g = 93% of the theoretical yield, and the yield after recrystallisation is 320 g = 80% of the theoretical yield.

The yields obtained in Example 1(b) are similar to those obtained in Example 1(a), i.e. hydrogen chloride and p-toluenesulphonic acid no not differ in their end effect in this case.

The pure m-compound, α,α'-bis-'2-hydroxy-3,5-dimethylphenyl)-m-diisopropylbenzene, has a melting point of from 190° to 191° C.

According to calculations based on gas chromatographic analysis, the ratio of isomers of the product prepared according to Example 1 corresponds to that of the biscarbinol put into the process.

EXAMPLE 2

A solution of 97 g (0.5 mol) of m/p-biscarbinol (ratio of isomers 3:2) in 382 g (2 mol) of o-cyclohexyl-p-cresol is added dropwise with stirring in the course of 6 hours to a mixture of 482 g (2 mol) of o-cyclohexyl-p-cresol and 350 ml of toluene which has been saturated with hydrogen chloride at room temperature, and at the same time the introduction of HCl is continued and the reaction temperature is maintained at from 20° to 22° C. The reaction mixture is left to stand overnight and subsequently heated to 50° to 60° C and hydrogen chloride, hydrochloric acid and excess cylcohexyl cresol are distilled off under vacuum. 240 g = 89% of the theoretical yield of a light colored residue are left behind. On addition of methanol, this residue crystallises to yield 170 g of product (melting point: from 153° to 172° C). The phenolic OH content is 6.2% (calculated 6.3%).

EXAMPLE 3

97 g (0.5 mol) of m/p-biscarbinol are reacted with 656 g (4 mol) of 2-tert.-butyl-p-cresol as described in Example 2, but in the presence of only 100 ml of toluene. After removal of the volatile constituents by distillation, particularly of excess butyl cresol, 239 g = 98% of the theoretical yield of a light coloured residue are obtained. This residue crystallises with mineral spirits to yield 195 g of product (melting point from 130° to 144° C), phenolic OH content 7.1% (calculated 7.0%). The ratio of isomers, which is found to be 6.5:3.5 lies within the limits of error of measurement of the biscarbinol used.

EXAMPLE 4

1200 parts of a copolyester of adipic acid, hexane-1,6-diol and 2,2-dimethylpropane-1,3-diol (molar ratio of diols 65:35) (molecular weight of copolyester 1950), 23.55 parts of N-methyl-bis-(β-hydroxypropyl)-amine, 342.65 parts of diphenylmethane4,4'-diisocyanate and 393 parts of anhydrous dimethylformamide are heated to from 45° to 50° C for 80 minutes to form the isocyanate prepolymer which has an isocyanate content of 3.06% (based on the solids content). (The polymer contains about 100 mVal of tertiary amino groups per kg).

70 parts of dry ice ($CO_2$) are added to 28.3 parts of 99.5% ethylene diamine in 3392 parts of dimethylformamide to form a fine carbamate suspension, and 1590 parts of the above-mentioned isocyanate prepolymer solution are then introduced within 4 minutes. The solution is pigmented with 4% of $TiO_2$ (rutile) (viscosity: 1230 poises/20° C). The solution is subsequently diluted with dimethylformamide to a solid concentration of 22.8% / 540 poises. The stabilizers are added to portions of the solutions, in each case dissolved in a small quantity of dimethylformamide.

The solutions are spun through a 16 aperture die (diameter 0.2 mm) by the dry spinning process, drawn off the spinning shaft at the rate of 100 m/min and wound on spools at the rate of 130 m/min. The filaments were dressed with talcum.

The measurements indicated in Table 1 were carried out on filaments which had been tempered for one hour at 130° C.

The effect of the stabilizers on the thermal properties of the filaments is shown in Table 2.

Dry spun filaments were in part subjected to a thermostability test and the reduction in molecular weight was measured as the $\eta_i$-value ($\eta_i = \ln \eta R/C$; $\eta R =$ relative viscosity; C = concentration in g/100 ml of hexamethylphosphoramide, measuring temperature = 25° C) (see Table 1). The filaments containing additives remained colourless when exposed to heat treatment at 180° C. (The values for tensile strength are given in g/dtex and for elongation at break in % in the following Tables).

hexane-1,6-diisocyanate, the solution has a viscosity of 700 poises/20° C. It is then subdivided into three portions as follows:
 a. without the addition of stabilizer
 b. with 1% of stabilizer 1a
 c. with 2% of stabilizer 1a
The solutions are spun by the dry spinning process.

Table 1
Heat stabilization by additives (filaments after dry spinning experiment)

| η 1 values | | original | after 30 sec/180° C | after 180 sec/180° C |
|---|---|---|---|---|
| with additive | | 1.10 | 1.09 (−0.9%) | 0.99 (Δ −10%) |
| + 2% | Stabilizer 1a | 1.10 | 1.10 (Δ ± 0%) | 1.052 (Δ −4.4%) |
| + 1% | of stabilizer 1a | 1.10 | 1.11 (Δ +0.9%) | 1.048 (Δ −4.8%) |
| + 1% | of UV stabilizer B (Tinuvin 327 Ciba/Geigy) | | | |
| + 1.5% | of stabilizer 1a | 1.10 | 1.09 (−0.9%) | 1.050 (Δ −4.5%) |
| + 1% | of UV stabilizer B (Tinuvin 327 Ciba/Geigy) | | | |
| + 1% | stabilizer 1a | 1.10 | 1.11 | 1.052 (−4.4%) |
| + 1% | of UV stabilizer C | | | |

Table 2
Effect of stabilizers on thermal properties of dry spun elastomer filaments

| | Ultimate tensile strength | Elongation at break | Heat distortion[a] Temperature (° C) | Heat tearing time[b] (seconds) |
|---|---|---|---|---|
| Without additive | 0.61 | 490 | 183.5 | 60.6 |
| + 1% of stabilizer 1a | 0.62 | 535 | 188.5 | 61.0 |
| + 1% of UV stabilizer B + 1.5% of stabilizer 1a | 0.63 | 527 | 185.5 | 67.5 |
| + 0.5% of UV stabilizer B + 2% of UV stabilizer B | 0.62 | 519 | 183.5 | 52.5 |

[a]The temperature at which a filament to which a weight of 1.8 mg/dtex has been suspended exceeds an elongation of 0.8% per ° C when heated at the rate of 2.1° per minute.
[b]Measurement of the time (seconds) at which a filament which has been stretched by 100% breaks off on a metal support 2.5 centimeters in width which is at a temperature of 193° C.

EXAMPLE 5

2000 parts of a copolyester of adipic acid, hexane-1,6-diol and 2,2-dimethylpropane-1,3-diol (molar ratio of diols 65:35) which has an average molecular weight of 2000 are mixed with 28.10 parts of N-methyl-bis-β-hydroxypropylamine (66 mVal of tert. amine/kg of solid substance) and a solution of 547.8 parts of diphenylmethane-4,4'-diisocyanate in 645 parts of dimethylformamide at 40° C and the mixture is reacted for 90 minutes at from 40° to 60° C to produce an isocyanate prepolymer (2.99% of isocyanate, based on the solid content).

3000 parts of the isocyanate prepolymer solution are stirred into a suspension of 110 parts of rutile and 56.40 parts of ethylene diamine in 8460 parts of dimethylformamide and 130 parts of solid carbon dioxide in the course of 5 minutes. After the addition of 7.2 parts of The draw-off rate is 250 m/min. Filaments with a titre of about 140 dtex are left to stand for 24 hours and then heat treated on rollers (temperature from 180° to 200° C) at a permitted shrinkage in German Offenlegungsschrift No. 1,660,294. The results of measurements carried out on filaments with and without the addition of stabilizer after exposure in a Xeno test for up to about 340 hours are shown in Table 3.

Table 3
Effect of stabilizers on the resistance to ultraviolet light exposure in the Xeno test of dry spun, thermally after-treated elastomer filaments (Filament titre about 160 dtex)

Discoloration, ultimate tensile strength and elongation at break after Xeno test exposure for x hours

| | without exposure | after 70 hours | after 143 hours | after 245 hours | after 340 hours |
|---|---|---|---|---|---|
| without stabilizer | 0.95/525 | 0.59/470 almost colourless | 0.30/375 yellowish | 0.16/270 yellow | 0.14/220 deep yellow |
| + 1% of stabilizer 1a | 1.00/515 | 0.96/480 colourless | 0.60/435 colourless | 0.37/375 colourless | 0.27/340 almost colourless to yellowish |
| + 2% of stabilizer 1a | 1.04/525 | 0.98/490 colourless | 0.93/490 colourless | 0.62/450 colourless | 0.37/350 almost colourless |

EXAMPLE 6

An elastomer spinning solution was prepared by the process according to Example 5 from 2000 parts of polyester (molecular weight 2000), 38.26 parts of N-methyl-bis-(β-hydroxypropyl)-amine (about 100 mVal of tert.amine/kg of solid substance) and 565.10 parts of diphenylmethane-4,4'-diisocyanate in 650 parts of dimethylformamide. These components were reacted to from an isocyanate prepolymer (3.00% isocyanate) and 3000 parts of this prepolymer were chain lengthened with 56.58 parts of ethylene diamine, 8461 parts of dimethylformamide, 140 parts of solid carbon dioxide and 7.76 parts of hexane-1,6-diisocyanate. The resulting spinning solution was mixed with 13 parts of acetic acid anhydride to remove any residual amino end groups and with 4%, by weight, of $TiO_2$ (in the solid substance).

The solution was divided up into portions to which the following stabilizers were added, and then spun by the conventional dry spinning process:
 a. without the addition of stabilizer
 b. with 2%, by weight, of stabilizer according to 1a
 c. with 1%, by weight, of stabilizer according to 1a and 1%, by weight, of UV stabilizer A
 d. with 1%, by weight, of stabilizer according to 1a and 1%, by weight, of UV stabilizer B
 e. with 2%, by weight, α,α'-bis-(2-hydroxy-3,5-dimethylphenyl)-m-diisopropylbenzene,m.p.:from 190°-191° C.

When elastomer filaments containing additive (e) (i.e. pure m-compound of the stabilizer) are warped on sectional beams, a large amount of additive which has been deposited on the surface of the filaments is rubbed off.
UV stabilizer A = "Tinuvin 320"/Ciba-Geigy
 [2-(2'-hydroxy-3',5'-di-tert.-butyl-phenyl)-benzotriazole] UV stabilizer B = "Tinuvin 327"/Ciba-Geigy
 [2-(2'-hydroxy-3',5'-di-tert.-butyl-phenyl)-5-chlorobenzotriazole]
UV stabilizer C =

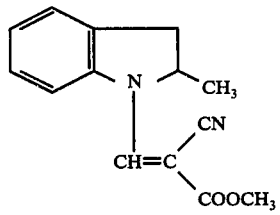

When 2% of stabilizers according to Example 2 or Example 3 is used, it is found that while the stabilizing effect is substantially the same as that obtained with the stabilizer according to Example 1(a), the stabilizers are even more readily soluble and they are very compatible with the polymers.

Table 4

Effect of stabilizers and of their mixtures with UV stabilizers on the resistance of dry spun elastomer filaments to UV exposure in the Xeno test
(Filament titre about 160 dtex)

Discoloration, ultimate tensile strength and elongation at break after Xeno test exposure for x hours

| | without exposure | after 305 hours |
|---|---|---|
| (a) without stabilizer | 0.85/515 | 0.25/364 yellow |
| (b) + 2% of stabilizer 1a | 0.81/515 | 0.48/460 colourless |
| (c) + 1% stabilizer 1a<br>1% of UV stabilizer A | 0.90/552 | 0.66/501 colourless |
| (d) + 1% of stabilizer 1a<br>1% of UV stabilizer B | 0.80/515 | 0.62/485 colourless |

EXAMPLE 7

600 parts of a copolyester of adipic acid, hexane-1,6-diol and 2,2-dimethylpropane-1,3-diol (molar ratio of diols 65:35) (molecular weight of copolyester 1615), 12 parts of N-methyl-bis-(β-hydroxypropyl)-amine, 169 parts of diphenylmethane-4,4-diisocyanate and 195 parts of dimethylformamide are heated with 2.38% of isocyanate (based on solid substances) to a temperature of from 50° to 54° C for 80 minutes to form an isocyanate preopolymer.

322.5 parts of the isocyanate prepolymer solution mentioned above and 4 parts, by weight, of $TiO_2$ (based on solid substance) are stirred into a solution of 11.8 parts of β-semicarbazido-propionic acid hydrazide in 23.6 parts, by weight, of water which has been heated to 50° C and diluted with 670 parts of dimethylformamide. A highly viscous elastomer solution (655 poises/20° C) is thereby obtained.

The solution was divided into portions to which the following stabilizers were added:
 a. no stabilizer
 b. 2% of stabilizer 1a
 c. 1% of stabilizer 1a
 d. 1% of stabilizer 1a + 1% of UV stabilizer B
 e. 2% of stabilizer II of German O No. 2,012,285, and the portions were cast to form films which were exposed in a Fadeometer.

While film (a) is yellow after only 22 hours, film (b) remains colourless for up to 66 Fadeometer hours. Film (c) begins to undergo discoloration after 66 Fadeometer hours, film (d) remains colourless like film (b) while film (e) begins to show slight discoloration after 30 Fadeometer hours and becomes increasingly yellow on further exposure up to 66 hours (comparison experiment).

When the samples are treated in boiling water for one hour on subjected to solvent extraction in boiling carbon tetrachloride for 15 minutes, the stabilizing effect is clearly better preserved in film (b). Substantial discoloration begins only after 66 Fadeometer hours while in comparison film (e) severe discoloration is seen after only 30 hours (in the case of solvent extraction). During the boiling treatment, the stabilizer in portion (e) migrates to the surface where it forms a deposit on the films. This is not observed in portions containing stabilizer (b) according to the present invention.

EXAMPLE 8

800 parts of polytetramethylene ether diol (molecular weight 1045) are reacted with 16.45 parts of N-methyl-bis-(β-hydroxypropyl)-amine and 285.9 parts of diphenylmethane-4,4-diisocyanate and 278 parts of dimethylformamide at a temperature of from 35° to 50° C for 40 minutes to form an isocyanate prepolymer with an NCO content of 2.09% (based on the solid content).

1. Chain lengthening with ethylene diamine:
5.24 parts of ethylene diamine and 895 parts of dimethyl formamide are converted into a carbamate suspension with 10 parts of solid carbon dioxide, and 440 parts of the prepolymer solution mentioned above are added within 3 minutes. The substance is then pigmented with 4% of $TiO_2$.

2. Chain lengthening with hydrazine hydrate:
4.37 parts of hydrazine hydrate are dissolved in 895 g of dimethylformamide and converted into the carbonate by the addition of 10 g of solid carbon dioxide. 425 parts of the above-mentioned isocyanate prepolymer solution are introduced within 3 minutes. The solution is then pigmented with 4%, by weight, of $TiO_2$ (rutile).

Portions of both solutions were treated with the following stabilizers:

a. no stabilizer b. 1%, by weight, of stabilizer 1a according to the present invention, + 1%, by weight, of light absorbing agent D c. 1%, by weight, of stabilizer 1a + 1%, by weight, of light absorbing agent D + 2%, by weight, of light absorbing agent according to Example 4 of German Patent Application P 25 20 814.4.

The solutions are then cast to form films and exposed in a Fadeometer.

D = light absorbing agent of the formula:

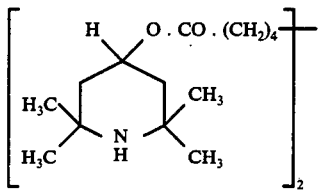

("Tinuvin 770" - Geigy/Ciba).

Whereas the unstabilized films were discoloured yellow after only 8 hours (film 1a) or 15 hours (film 2a) and had no mechanical strength (less than 0.08 g/dtex) after from 22 to 30 hours exposure in the Fadeometer and showed severe crazing on the surface, the exposed films were still colourless after 66 Fadeometer hours (the test was stopped at this point), they showed no signs of degradation or loss of elasticity and no crazing effect on the surface. Such stabilization of polyether ureas, which are very sensitive substances, must be regarded as excellent.

EXAMPLE 9

600 parts of a hexane-1,6-diol polycarbonate (molecular weight 1925) having OH number 58.25 are heated to 97° C together with 138.5 parts of 1-isocyanatomethyl-3,5,5-trimethylcyclohexane and 185.5 parts of the aromatic hydrocarbon mixture "Solvesso 100" (Manufactured by Shell) for about 220 minutes. A prepolymer solution having an isocyanate content of 3.58% (in the solid substance) is obtained.

4.2 parts of diaminocyclohexane (17.3% of cisisomer and 82.7% of trans-isomer) in 233 parts of Solvesso/ethylene glycol (1:1) are introduced into a reaction vessel and 107.5 parts of the prepolymer solution are added with stirring. A homogeneous solution which is stable in storage and has a viscosity of 266 poises/20° C is obtained.

The films are cut up into threads and exposed in a Fadeometer.

The alihatic polyurethane (used for dressings or coating compounds) remains colourless even after prolonged exposure to light, in contrast to aromatic polyurethanes, but it suffers a loss in tensile strength. Degradation is considerably slowed down by the addition of stabilizer according to the present invention.

Table 5

|  |  | Original | 154 hours exposure time of cut threads in the Fadeometer |
|---|---|---|---|
| RF (g/dtex) | without stabilizer | 0.69 | 0.29 |
| discoloration |  | colourless | colourless |
| RF (g/dtex) | + 2% of stabilizer 1a | 0.69 | 0.63 |
| discoloration |  | colourless | colourless |

RF* = ultimate tensile strength.

EXAMPLE 10

The following are incorporated in portions of the elastomer solution which has been pigmented with $TiO_2$ according to Example 4:

a. no stabilizer b. 2% of stabiliser 4 according to German Patent application No. P25 20 814.4 c. 2% of stabilizer 4 according to German Patent appliction P25 20 814.4 + 1% of stabilizer 1a (according to the present invention)

d. 2% of stabilizer 4 according to German Patent application P 25 80 814.4 + 2% of stabilizer 1a (according to the present invention).

The portions of solution are then cast to form films and the films are cut up into rectangular threads (about 280 dtex) which are all exposed to a Fadeometer at the same time.

Table 6 shows the improvement in colour stability and preservation of the mechanical-elastic values (ultimate tensile strength and elongation at break). It may be seen that the addition of stabilizers according to the present invention may produce a marked increase in the effect of the stabilizers according to German Patent Application P 25 20 814.4.

Table 6

Ultimate tensile strength, elongation at break and discoloration of cut polyester urethane urea elastomer threads after exposure in the Fadeometer

|  | without exposure | after 8 hours | after 22 hours | after 44 hours | after 66 hours |
|---|---|---|---|---|---|
| (a) without stabilizer | 0.59/628 | 0.45/590 yellow | 0.11/365 deep yellow | 0.07/140 deep yellow | — |
| (b) + 2% of stabilizer 4 according to P 25 20 814.4 | 0.58/617 | 0.56/605 colourless | 0.45/592 almost colourless | 0.29/525 yellowish to yellow | 0.09/350 yellow |
| (c) + 2% of stabilizer 4 according to P 25 20 814.4 + 1% of stabilizer 1a (according to the present invention) | 0.56/622 | 0.56/625 colourless | 0.54/625 colourless | 0.51/625 colourless | 0.39/574 almost colourless |
| (d) + 2% of stabilizer 4 according to P 25 20 814.4 + 2% of stabilizer 1a (according to the present invention) | 0.65/652 | 0.62/647 colourless | 0.52/645 colourless | 0.54/635 colourless | 0.40/590 colourless |

What we claim is:

1. A mixture comprising at least 20 %, by weight, of an α,α'-bis-(2-hydroxy-3,5-dialkylphenyl)-m-diisopropylbenzene and an α,α'-bis-(2-hydroxy-3,5-dialkyl-phenyl)-p-diisopropyl-benzene.

2. A mixture as claimed in claim 1 which comprises from 40 to 70 %, by weight, of the said m-compound.

3. A mixture as claimed in claim 1 which comprises α,α'-bis-(2-hydroxy-3,5-dimethylphenyl)-m-diisopropylbenzene and α,α'-bis-(2-hydroxy-3,5-dimethylphenyl)-p-diisopropylbenzene.

4. A process for the preparation of a mixture as claimed in claim 1 which comprises reacting a mixture of α,α'-dihydroxy-m- and -p-diisopropylbenzenes with an excess of 2,4-dialkylphenols which may be further substituted in the presence of hydrogen chloride which is not bound to water.

5. A process as claimed in claim 4 in which the molar ratio of α,α'-dihydroxy-diisopropylbenzene : dialkylphenol is at least 1 : 3.

6. A process as claimed in claim 5 in which the said ratio is from 1 : 5 to 1 : 12.

7. A process as claimed in claim 4 in which the reaction temperature is from 0° to 100° C.

8. A process as claimed in claim 7 in which the said temperature is from 20° to 70° C.

* * * * *